US00PP12267P2

(12) United States Plant Patent
Olesen et al.

(10) Patent No.: US PP12,267 P2
(45) Date of Patent: Dec. 11, 2001

(54) SHRUB ROSE VARIETY 'POULNINGA'

(75) Inventors: L. Pernille Olesen; Mogens N. Olesen, both of Fredensborg (DK)

(73) Assignee: Poulsen Roser APS, Fredensborg (DK)

( * ) Notice: Subject to any disclaimer, the term of this patent is extended or adjusted under 35 U.S.C. 154(b) by 0 days.

(21) Appl. No.: 09/287,290

(22) Filed: Mar. 31, 1999

(51) Int. Cl.[7] ..... A01H 5/00
(52) U.S. Cl. ..... Plt./102
(58) Field of Search ..... Plt./102, 107, 109

*Primary Examiner*—Howard J. Locker

(57) ABSTRACT

A new garden rose plant which has abundant, soft yellow and red-purple striped flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between two undistributed, unnamed seedlings. The two parents were crossed and the resulting seeds were planted in a controlled environment. The new variety is named 'POULninga'.

The new rose may be distinguished from its seed parent, an unnamed seedling created by the same inventors, by the following combination of characteristics:

1. The seed parent is a floribunda and 'POULninga' is classified as a shrub rose;

2. The blooms of the seed parent are orange-red in color; whereas 'POULninga' has striped-yellow and red-purple blooms;

3. The seed parent has double petalage; whereas, 'POULninga' has semi-double petalage.

The new variety may be distinguished from its pollen parent, an unnamed seedling created by the same inventors, by the following combination of characteristics:

1. The pollen parent is classified as a miniature rose and is a much smaller shrub than 'POULninga';

2. The pollen parent also has striped flowers, but the colors are red, white and a limited amount of pink striping.

The objective of the hybridization of this rose variety for nursery and garden use was to create a new and distinct variety with unique qualities, such as:

1. Uniform and abundant flowers;
2. Vigorous, compact growth;
3. Disease resistance;
4. Continual blooming;
5. Striped flowers.

This combination of qualities is not present in previously available commercial cultivars of this type and distinquishes 'POULninga' from all other varieties of which we are aware.

As part of their rose development program, L. Pernille Olesen and Mogens N. Olesen germinated the seeds from the aforementioned hybridization and conducted evaluations on the resulting seedlings in a controlled environment in their nursery in Fredensborg, Denmark.

'POULninga' was selected in spring 1988 by the inventors as a single plant from the progeny of the aforementioned hybridization.

Asexual reproduction of 'POULninga' by traditional budding was first done by L. Pernille and Mogens N. Olesen in August 1988. This initial and other subsequent propagations conducted in controlled environments have demonstrated that the characteristics of 'POULninga' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULninga'. Specifically illustrated in SHEET 1:

1. Stem showing branching and the attachment of leaves, buds, and peduncles;

2. Flower bud, partially opened bud, and open bloom;

3. Flower petals, detached;

4. Sepals and pedicel;

5. Flowering stem as well as a bare stem exhibiting thorns;

6. Leaves.

DETAILED DESCRIPTION OF THE VARIETY

The following is a description of 'POULninga', as observed in its outdoor growth in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULclimb', a climbing rose variety from the same inventors described and illustrated in U.S. Plant Pat. No. 10,639 and issued on Oct. 13, 1998 are compared to 'POULninga' in Chart 1.

CHART 1

| | 'POULninga' | 'POULclimb' |
|---|---|---|
| Color of upper surface | Variably striped in Yellow Group 10A– | Stripes as light as 159D and 11D |

CHART 1-continued

| | 'POULninga' | 'POULclimb' |
|---|---|---|
| of open bloom. | 10D with Red-Purple Group 66B–D. | and as dark as between 58B and 60D. |
| Petalage. | Semi-double, 12–14 petals. | Semi-double, 10–15 petals. |
| Height of plant. | 100–150 cm. | 300–350 cm. |

Parents:

*Seed parent.*—Unnamed seedling.

*Pollen parent.*—Unnamed seedling.

Classification:

*Botanical.*—*Rosa hybrida.*

*Commercial.*—Shrub.

FLOWER AND FLOWER BUD

Blooming habit: Recurrent to nearly continuous.

Flower bud:

*Size.*—Upon opening, 24 mm–26 mm in length from base of receptacle to end of bud.

*Bud form.*—Pointed ovoid.

*Bud color.*—As sepals unfold, irregular strips and splashes of Yellow-White Group 158C, Yellow-Group 9B–9C, Red-Purple Group 63B–63C, Red Group 50A–53D. Background of Yellow Group 8B–8C at ¼ opening.

*Sepals.*—Yellow-Green Group 144A. Weak foliaceous appendages, with some flowers with a less develped smaller sixth sepal. Stipitate glands on margins.

*Receptacle.*—Surface: Smooth with a few short fine white hairs. Shape: Funnel shape. Color: Yellow-Green Group 143B.

*Peduncle.*—Surface: Smooth with many stipitate glands. Length: 35–45 mm average length. Color: Yellow-Green Group 144B.

*Strength.*—Erect to nearly horizontal.

*Borne.*—3 to 5 buds per flowering stem. Flowers opening uniformly. Pedicel is typically 20–30 mm in length.

Flower bloom:

*Fragrance.*—Light floral fragrance.

*Duration.*—The blooms have a duration on the plant of approximately 4 to 5 days. Petals fall cleanly away from plant.

*Size.*—Average flower diameter is 75–80 mm when open.

*Form.*—Shape of flower when viewed from the side: Upon opening, upper part: Convex. Upon opening, lower part: Convex. Open flower, upper part: Flattened convex. Open flower, lower part: Flat.

*Petalage.*—Semi-double with 12–14 petals with 2–4 petaloids.

Color:

*Upon opening, petals.*—Outermost petals: Upper Surface: Stripes of Yellow and Red-Purple. Basal zone has Yellow stripes of Yellow Group 10A–B. Middle zone — Yellow Group 10C–10D. Marginal zone — Yellow Group 10D. Limited stripes of Red-Purple Group 65C–65D. In basal area there are stripes of Red-Purple Group 66A changing to Red-Purple Group 66B on mid-petal to marginal zone. Reverse Side: Basal — Yellow Group 9A–9B to 10C–10D. Stripes of Red-Purple Group 66C–66D.

*Upon opening, basal petal spots.*—Outer Side: At point of attachment, Yellow Group 12A changing in basal area to Yellow Group 10A. Inner Side: Yellow Group 12A.

*After opening, petals.*—Outermost petals: Stripes of Yellow to Cream Yellow with Red-Purple. Basal zone to middle zone is Yellow Group 10B–10C; middle zone to marginal zone — Yellow Group 10C–10D. Stripes of Red-Purple in the basal zone to middle zone are Red-Purple Group 66A–66B. Stripes in middle zone to marginal zone Red-Purple Group 66B–66C and Red-Purple Group 65D. Reverse Side: Basal zone generally Yellow Group 9B–9C with middle and marginal zones expressing limited to no stripes in Red-Purple Group 68C–68D.

*After opening, distinctive basal petal spots.*—Outer Side: At point of attachment, Yellow Group 12B. Basal zone is Yellow Group 10A–B. Inner Side: Yellow Group 12B.

Petals:

*Petal reflex.*—Petals reflex slightly.

*Petal edge.*—Ruffled.

*Shape.*—Round.

*Petaloids.*—2–4.

*Texture.*—Thick with a velvet feel.

*Arrangement.*—Informal.

Reproductive organs:

*Pollen.*—Color: Yellow Group 13B. Quantity: Prolific producer of pollen.

*Anthers.*—Size: Small. Quantity: Abundant.

*Filaments.*—Color: Yellow Group 9B with some intonations of Greyed-Red Group 79A.

*Stigmas.*—At same position as anthers. Color: Yellow-Green Group 145D.

*Styles.*—Color: Green-White Group 157B. Intonations: Immediately below stigma, intonations of Red-Purple Group 63C.

*Hips.*—None observed.

PLANT

Plant growth: Vigorous, upright to bushy, and arching. Basal canes to 20 mm in diameter. When grown as a budded field grown plant on *Rosa multiflora* understock, the average height of the plant itself is 100–150 cm and the average width is 100 cm.

Stems: Produces strong basal canes up to 20 mm in diameter.

*Color.*—Young wood: Yellow-Green Group 144B. Older wood: Yellow-Green Group 147C.

*Thorns.*—Incidence: Moderate. Size: Average length: 7 mm–8 mm. Color: Yellow-Green Group 145C, with immature thorns having intonations of Greyed-Red Group 179B. Shape: Concave with downward curve.

*Surface.*—Young wood: Smooth. Older wood: Smooth.

Plant foliage: Normal number of leaflets on leaves in middle of the stem: 5 leaflets.

*Leaf size.*—115–125 mm (l)×80–90 mm (w).

*Quantity.*—Above average abundance.

*Color.*—Upper Leaf Surface: Green Group 137A to Yellow-Green Group 147A. Lower Leaf Surface: Yellow-Green Group 146D. Juvenile foliage: Upper Surface: Green Group 137A, with intonations of Greyed-Red Group 181A. Lower Surface: Green Group 137B, with intonations of Greyed-Red Group 181A. Anthocyanin intonation: Location: All parts of upper plant. Color: Greyed-Red Group 181A.

Plant leaves and leaflets:

*Stipules.*—Size: 15 mm–18 mm. Color: Green Group 143A. Stipitate glands: Located on margins.

*Petiole.*—Length: 20 mm–30 mm. Color: Green Group 137C. Underneath: Smooth. Margins: Limited numbers of stipitate glands and fine white hairs.

*Rachis.*—Color: Green Group 137C. Underneath: Smooth, with a few small prickles. Margins: With stipitate glands and fine white hairs.

*Leaflet.*—Edge: Serrated. Shape: Ovate. Texture: Glossy and leathery leaflets.

Disease resistance: Above average resistance to mildew, rust, and black spot under normal growing conditions in Jackson County, Oreg.

Cold hardiness: 'POULninga' is found to be cold hardy in Denmark and in Jackson County, Oreg.

We claim:

1. A new and distinct variety of rose plant of the shrub class, substantially as herein illustrated and described as a distinct and novel rose variety due to its abundant, yellow and red-purple striped flowers, vigorous growth, disease resistance, and extended period of bloom.

* * * * *

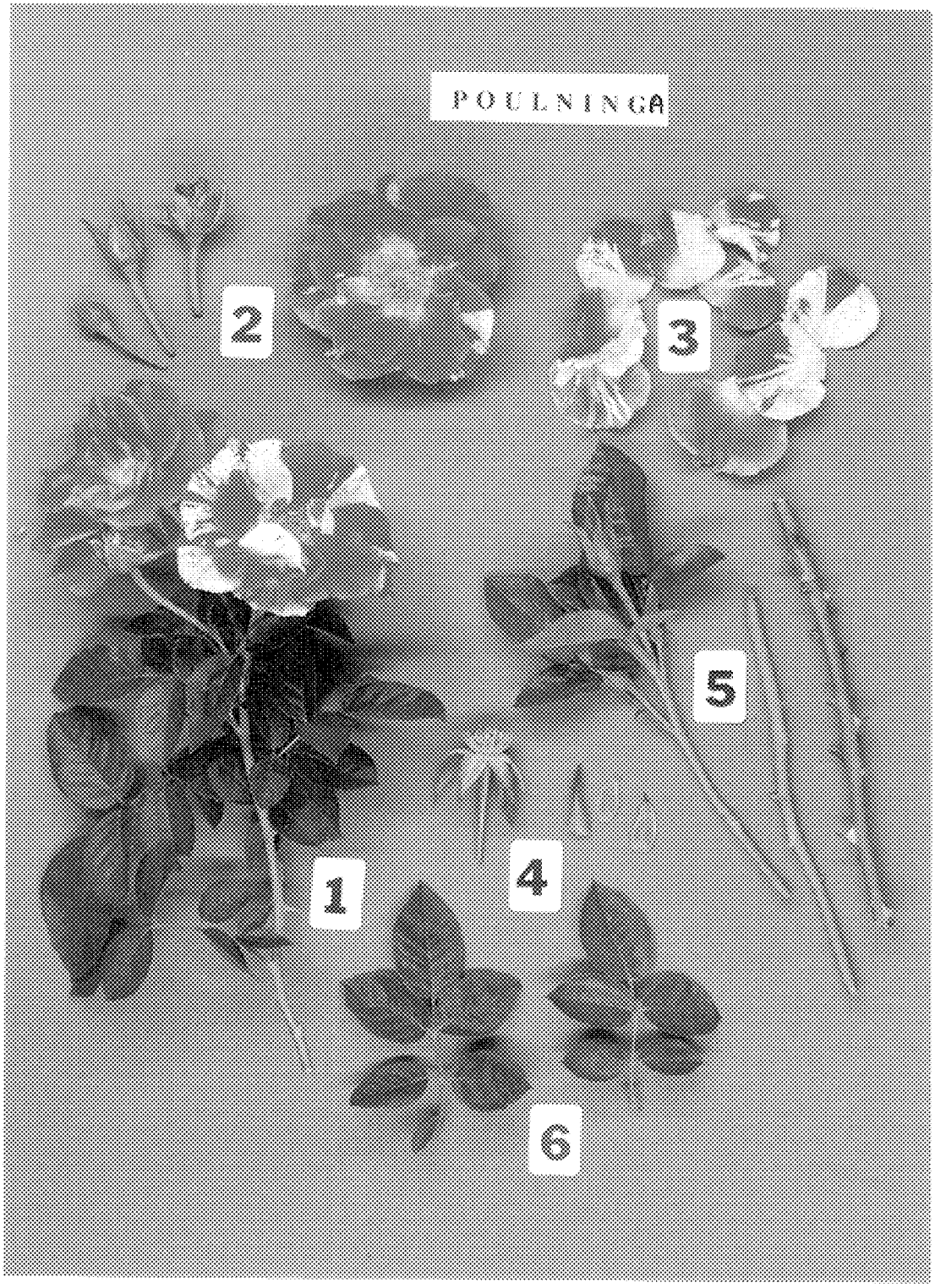
POULNINGA
2
3
5
1
4
6